United States Patent
Zhang et al.

(10) Patent No.: US 9,081,082 B2
(45) Date of Patent: Jul. 14, 2015

(54) SYSTEM AND METHOD FOR WIRELESS DETECTOR APPLICATION IN MEDICAL SYSTEMS

(75) Inventors: Xinyu Zhang, Beijing (CN); Bin Ye, Beijing (CN)

(73) Assignee: GE Medical Systems Global Technology Company, LLC, Waukesha, WI (US)

( * ) Notice: Subject to any disclaimer, the term of this patent is extended or adjusted under 35 U.S.C. 154(b) by 462 days.

(21) Appl. No.: 13/299,866

(22) Filed: Nov. 18, 2011

(65) Prior Publication Data

US 2013/0127613 A1    May 23, 2013

(51) Int. Cl.
  *G08B 1/08* (2006.01)
  *G01S 5/14* (2006.01)
  *A61B 6/00* (2006.01)
  *G01S 5/02* (2010.01)

(52) U.S. Cl.
  CPC .............. *G01S 5/14* (2013.01); *A61B 6/4494* (2013.01); *A61B 6/547* (2013.01); *A61B 6/563* (2013.01); *G01S 5/0252* (2013.01)

(58) Field of Classification Search
  CPC .......... A61B 6/00; A61B 6/44; A61B 6/4494; A61B 6/54; A61B 6/547; A61B 6/56; A61B 6/563; A61B 6/566; G01S 5/00; G01S 5/0009; G01S 5/0036; G01S 5/02–5/0231; G01S 5/04; G01S 5/06; G01S 13/06; G01S 13/08; G01S 3/00; G01S 3/02; G01S 3/14; G01S 3/46; G01S 3/50

USPC .............. 340/10.1–10.6, 572.1–572.9, 539.1, 340/0.11, 0.12, 0.21, 0.16, 0.14; 455/115.3, 455/513

See application file for complete search history.

(56) References Cited

U.S. PATENT DOCUMENTS

| | | | | |
|---|---|---|---|---|
| 5,588,005 | A * | 12/1996 | Ali et al. | 370/346 |
| 5,895,436 | A * | 4/1999 | Savoie et al. | 701/468 |
| 6,707,880 | B2 * | 3/2004 | Yamayoshi | 378/92 |
| 6,773,396 | B2 * | 8/2004 | Flach et al. | 600/300 |
| 6,856,609 | B2 * | 2/2005 | Kusaka et al. | 370/331 |
| 7,242,306 | B2 * | 7/2007 | Wildman et al. | 340/573.1 |
| 7,567,651 | B2 | 7/2009 | Serceki et al. | |
| 7,639,131 | B2 * | 12/2009 | Mock et al. | 340/539.3 |
| 7,880,616 | B2 * | 2/2011 | Kanagala et al. | 340/572.1 |
| 8,150,477 | B2 * | 4/2012 | Cho et al. | 455/574 |
| 2001/0011954 | A1 * | 8/2001 | Shelton et al. | 340/825.49 |
| 2007/0132577 | A1 * | 6/2007 | Kolavennu | 340/539.13 |
| 2008/0228962 | A1 * | 9/2008 | Ong | 710/35 |
| 2008/0259897 | A1 | 10/2008 | Van Helvoort et al. | |
| 2009/0267737 | A1 * | 10/2009 | Kawaguchi et al. | 340/10.1 |
| 2010/0198999 | A1 * | 8/2010 | Nair et al. | 710/33 |
| 2010/0234720 | A1 | 9/2010 | Tupin, Jr. et al. | |
| 2011/0148602 | A1 * | 6/2011 | Goh et al. | 340/10.41 |

* cited by examiner

*Primary Examiner* — Steven Lim
*Assistant Examiner* — Ryan Sherwin
(74) *Attorney, Agent, or Firm* — Armstrong Teasdale LLP

(57) ABSTRACT

A system for wireless detector application in a medical system is provided. The system includes at least three host wire adapters configured to receive beacon messages broadcast periodically by a wireless detector, and obtain information about the wireless detector based on the received beacon messages. The system further includes a controller configured to receive information about the wireless detector from the at least three host wire adapters, and determine a position of the wireless detector based on the received information.

18 Claims, 3 Drawing Sheets

SYSTEM AND METHOD FOR WIRELESS DETECTOR APPLICATION IN MEDICAL SYSTEMS

CROSS REFERENCE TO RELATED APPLICATIONS

This application claims the benefit of Chinese Patent Application No. 201010564953.2 filed Nov. 18, 2010, which is hereby incorporated by reference in its entirety.

BACKGROUND OF THE INVENTION

The present invention relates to a medical system, in particular to the positioning and management of wireless detectors in medical systems.

In recent years, imaging modes such as X-ray imaging mode have made breakthroughs in terms of image transmission between the wireless detector and the medical system by updating wired communication into wireless communication. However, the application of ultra wide band (UWB) wireless detectors also bring about some potential issues to medical systems, for example poor wireless link quality, limited signal coverage and difficulty in management of multiple detectors.

Such potential issues arise because of the characteristics of the UWB technique. First, to get a better radio coexistence, the UWB signal strength is extremely low, with the maximum of −41.3 dBm/MHz. Second, the UWB transmission speed could be up to 1 Gbps because of the high frequency characteristic, so the multiple path effect is very obvious and signal is degraded and interfered at the receiver. Thus the physical limitation for UWB communication is 10 meters, and the signal has a poor performance around obstacles and is easy to be blocked in a Non-Line-of-Sight (NLOS) environment. In hospital application, it is very challenging to communicate with the wireless detectors when the antenna of the host wire adapter is installed in a NLOS position. Or for a patient with large size, signal might be broken in the stretcher table or in the wheelchair. The consequences of these potential issues are poor wireless signal quality and low image transmission speed. The current solution adopted is usually to change the detector from a wireless mode to a wired mode.

In the case where there are multiple wireless detectors, since these wireless detectors can be located anywhere, it is hard to locate the target detector. The existing solution is to disable all the wireless detectors except for the target detector. However, this solution is very complicated and causes many inconveniences to the users and the system designers.

Therefore, there is the need for a system and method for wireless detector application in medical systems so as to solve the above technical problems.

SUMMARY OF THE INVENTION

To solve the above-mentioned problems, such as the limited wireless coverage, poor link quality and complicated procedures of management of multiple wireless detectors, the embodiments described herein provide a system and method for wireless detector application in medical systems.

A system for wireless detector application in medical systems includes at least three host wire adapters for receiving beacon messages broadcast periodically by a wireless detector and obtaining information about the wireless detector based on the received beacon messages, and a controller for receiving information about the wireless detector from the at least three host wire adapters and determining the position of the wireless detector based on the received information.

A method for wireless detector application in medical systems includes at least three host wire adapters obtaining information about a wireless detector based on the beacon messages broadcast periodically by the wireless detector, and determining the position of the wireless detector based on the information about the wireless detector from the at least three host wire adapters.

By means of the system and method for wireless detector application in medical systems as described herein, the following advantages can be realized:

obtaining stronger wireless signals and larger signal coverage, and reducing the "signal blind area" in the medical treatment room to the minimum;

more accurate UWB positioning as compared to the existing positioning solutions including WiFi, RFID, Bluetooth, ultrasound, indoor-GPS;

tracking moveable components in the medical treatment room with high resolution (millimeter in theory but centimeter in practice) and real-time response (microsecond in theory but millisecond in practice);

easier management of multiple wireless detectors, which reduces the burdens on the users and the system designers; and safer exposure and image transmission, which avoids the problem that the image of the target detector is not transmitted.

BRIEF DESCRIPTION OF THE DRAWINGS

A more thorough understanding of the embodiments described herein will be achieved by referring to the detailed descriptions of the specific embodiments below in conjunction with the drawings.

DETAILED DESCRIPTION OF THE INVENTION

Usually, a fixed table, a fixed wall stand and a distribution cabinet are installed in a medical treatment room in addition to a radiation source (e.g. X-ray tube), and the medical treatment room is usually an open space for portable applications including, but not limited to, stretchers and wheelchairs. The embodiments described herein will be described in detail below taking the X-ray diagnostic system as an example. However, it shall be noted that the embodiments described herein are not limited only to the X-ray diagnostic system, but can also be applied to other medical systems that use wireless detectors.

Figure 1A:
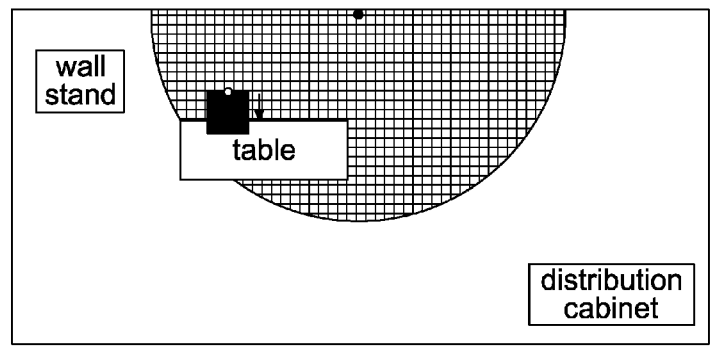
FIG. 1a shows a schematic view of a range of a signal coverage of a single host wire adapter (HWA) system.

As shown in FIG. 1a, in the X-ray exposure room, a single HWA is installed on the wall that is opposite to the direction of the insertion of the wireless detector so as to achieve a better signal coverage. The white dot in FIG. 1a shows the position of the wireless detector, the arrow shows the direction of insertion of the wireless detector, and the black dot shows the position of the single HWA. When the distance is greater than 3 meters, the signal coverage degrades 3 dB, as shown by the cross-hatched area.

In order to enlarge the range of signal coverage, the embodiments described herein provide a multiple-HWA in which multiple HWAs are installed in the medical treatment room such as the X-ray exposure room. The multiple HWAs can be located anywhere, but in some embodiments, the distance between every two HWAs may be smaller than a predetermined value, such as, for example 5 meters. In addition, in some embodiments, the positions of the multiple HWAs are at least 0.5 meters away from a metal obstacle.

Figure 1B:
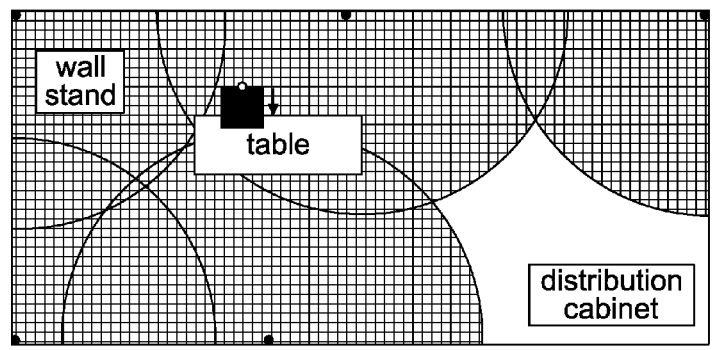
FIG. 1b shows a schematic view of a range of a signal coverage of a multiple-HWA system.

As shown in FIG. 1b, five HWAs are installed in the X-ray exposure room, wherein at least one HWA is installed on the wall opposite to the insertion direction of the wireless detector. The white dot in the figure shows the position of the wireless detector, the arrow shows the insertion direction of the wireless detector, and the black dots show the positions of the five HWAs. As indicated by the cross-hatched area in FIG. 1b, the range of signal coverage is greatly increased without a degradation of 3 dB.

In the exemplary embodiment, the multiple HWAs may be arranged at corners of the X-ray exposure room, 2 to 3 meters from the floor and at least 0.3 meters from the ceiling. To achieve a better range of coverage within the room, the angle of the antenna may be adjusted appropriately. The way of arrangement is very important for the multiple-HWA system, and the performance of the multiple-HWA system is closely related to the position and angle of installation of the antenna. To avoid system performance difference caused by installation, a fixed tag will be introduced into the multiple-HWA system for automatic calibration.

According to the requirement of the wireless Universal Serial Bus (USB) that defines application layer specification of the UWB communication, there is only one wireless host controller in any wireless USB system. Each wireless host controller can support 127 devices at most. In the multiple-HWA system of the embodiments described herein, a HWA serves as the wireless host controller, and the plurality of wireless detectors serve as devices. Therefore, since multiple HWAs are installed in the X-ray exposure room, only one HWA is used for image transmission and beacon exchange, which is called as the active HWA.

The process of selecting the active HWA is called an optimal signal creation process. The process starts after the radiologist has positioned the patient and the process is initialized by pressing a button on the overhead tube suspension (OTS) or on some handheld device. After the radiologist leaves the X-ray exposure room and closes the door, the optimal signal creation process will be finished and ready for exposure. The whole process lasts less than 1 second.

The optimal signal creation process will be specifically described below. In this process, the wireless detector periodically broadcasts beacon signals and each HWA will receive said beacon signals and obtain the Received Signal Strength Indicator (RSSI) and the Link Quality Indicator (LQI). Since each HWA is at a different position, the values of RSSI and LQI for all the HWAs are different. The multiple HWAs are connected to a Single Board Controller (SBC) through a USB expansion wire. The SBC serves as the USB hub and the central controller of the multiple HWAs. Each HWA reports the values of RSSI and LQI to the SBC. Then, the SBC will arbitrate the values and select the largest value representing the optimal wireless signal condition. In some embodiment, the RSSI and LQI values within a few milliseconds may be averaged to obtain the stable performance. Next, the SBC will assign the HWA having the largest RSSI and LQI values to be the active HWA. Later, commands and images will be transmitted through the active HWA, and the rest of the HWAs will automatically enter a sleep mode. Upon completion of the optimal signal creation process, the process will automatically be ready for exposure. The active HWA will remain the active HWA until the button on the OTS is pressed again.

If the active HWA is within the Non-Line-Of-Sight (NLOS) range of the wireless detector, it is possible to switch the active HWA to a HWA that is within the Line-Of-Sight (LOS) range of the wireless detector. In this way, the poor link quality caused by NLOS can be improved significantly. According to the signal strength received by each HWA from the wireless detector, the HWA corresponding to the largest received signal strength is selected to be the active HWA. In operation, all HWAs are connected to a controller, and the HWAs will periodically report to the controller the signal strengths they currently received from the wireless detector. The controller will compare all the signal strengths to determine which is the largest and switch the currently active HWA to the HWA having the largest signal strength value.

Figure 2:
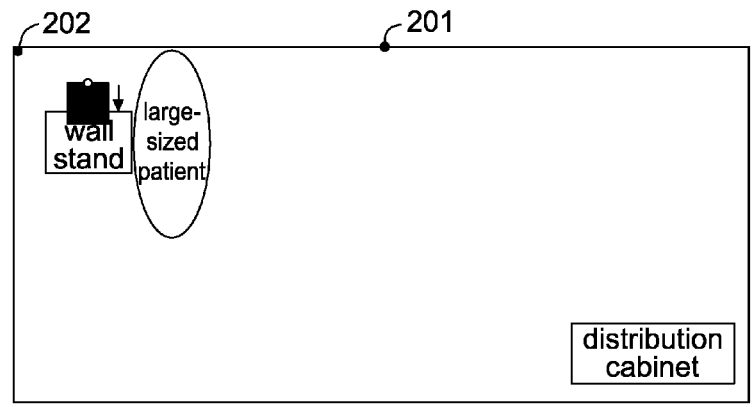
FIG. 2 is a schematic view of an exemplary embodiment of switching an HWA.

As shown in FIG. 2, when a large-sized patient is standing before the wall stand, the body covers the handle of the wireless detector, where the wireless panel is located. For the existing X-ray systems, the HWA and the antenna will be at position 201. The patient is between HWA 201 and the wireless detector installed in the wall stand, which puts the HWA 201 within the NLOS range of the wireless detector, so the link quality will degrade. In this case, if the system switches to HWA 202, the link quality will improve significantly.

Figure 3:
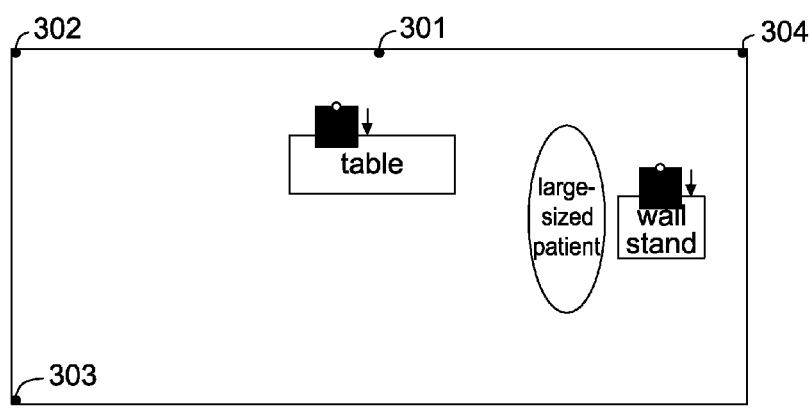
FIG. 3 is a schematic view of an exemplary embodiment of improving a wireless link quality.

As shown in FIG. 3, HWA 301 may be optimal for the table application, HWA 304 may be optimal for the wall stand application, and HWA 302 and HWA 303 may be optimal for such portable application as a stretcher or a wheelchair.

By means of the multiple-HWA system provided by the present application, management of wireless detectors may be improved. The wireless detectors may be managed according to their position feedback.

Now it will be described in detail how to determine the positions of the wireless detectors.

Generally, the positioning system is constructed on the basis of the distance measurement technique, so the distance measurement theory will be introduced first and then the geometric positioning.

Distance Measurement Theory

The UWB distance measurement for multiple-HWA is implemented on the basis of the rotation signal sub-space (RSS) theory. Based on some channel characteristics, the RSS measurement provides information about the distance between two nodes. The main idea of the RSS-based method is that if the relation between the distance and the power loss is known, and the transmission power is known, then the RSS measurement performed at one node can be used to estimate the distance between the node and the transmission node. The relation between the RSS power and the distance is as shown in equation (1). The ideal case is that the average RSS on a long enough time interval will eliminate the influences from multi-path attenuation and shadow effect, and the following model will be obtained:

$$\overline{P}(d) = P_0 - 10n \log_{10}(d/d_0) \quad (1)$$

wherein, n is the index of path loss (PL), $\overline{P}(d)$ is the average received power (dB) at distance d, and $P_0$ is the received power (dB) at a reference distance $d_0$.

Geometric Positioning

Figure 4:
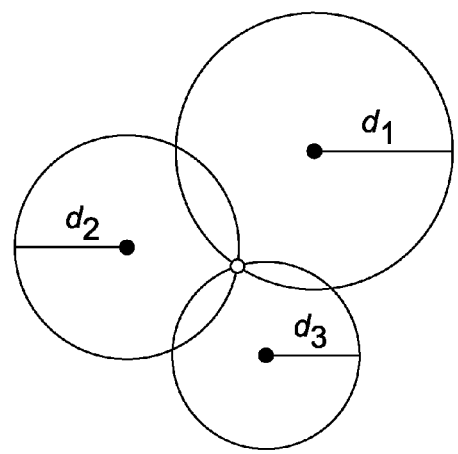
FIG. 4 is a schematic view of an exemplary embodiment of using trilateration for two-dimensional positioning.

The geometric positioning technique solves the position of the target node by measuring, on the basis of RSS or the time of arrival (TOA), the intersection of the position lines obtained from a group of distance measurement performed at a plurality of reference nodes. The target node may be located on the tracks of the circles having the reference nodes as their centers and with the results of distance measurement as their radiuses. Then, the intersection of the tracks of the circles will be the target position. FIG. 4 is a schematic drawing of the principle of using trilateration for two-dimensional positioning. The reference nodes (indicated by black dots in the figure) measure their distance from the target node (indicated by the white dot in the figure) by means of RSS or TOA estimation, which results in three circles that pass through the target node. The intersections of these three circles may be calculated to obtain the position of the target node, which is called trilateration.

For a three-dimensional positioning, at least four reference nodes are needed, and the position information thereof are represented as $(x_i, y_i, z_i)$, for $i=1, 2, 3, 4$. Suppose that $d_1$, $d_2$, $d_3$, $d_4$ represent the distance measurements measured from four RSS. Then the four equations given below must be used jointly for a solution so as to estimate the position of the target node using trilateration:

$$d_i = \sqrt{(x_i-x)^2+(y_i-y)^2+(z_i-z)^2}, i=1,2,3,4 \qquad (2)$$

wherein, $(x_i, y_i, z_i)$ is the known position of the $i^{th}$ reference node, and $(x, y, z)$ is the position of the target node.

A transformation is made to equation (2) to obtain the following equation:

$$(x_i-x)^2+(y_i-y)^2+(z_i-z)^2=d_i^2 \qquad (3)$$

Paired subtraction is performed in equation (3):

$$\begin{cases} (x_1-x_2)x+(y_1-y_2)y+(z_1-z_2)z = \frac{1}{2}[(x_1^2+y_1^2+z_1^2)-(x_2^2+y_2^2+z_2^2)+d_2^2-d_1^2] \\ (x_2-x_3)x+(y_2-y_3)y+(z_2-z_3)z = \frac{1}{2}[(x_2^2+y_2^2+z_2^2)-(x_3^2+y_3^2+z_3^2)+d_3^2-d_2^2] \\ (x_3-x_4)x+(y_3-y_4)y+(z_3-z_4)z = \frac{1}{2}[(x_3^2+y_3^2+z_3^2)-(x_4^2+y_4^2+z_4^2)+d_4^2-d_3^2] \end{cases} \qquad (4)$$

The number of the unknown parameters is represented as n, and the number of the equations is represented as m. If the positions of four reference nodes are known, then the number of the unknown parameter equals to the number of the equations (m=n). Thus a unique solution can be obtained for equation (4).

Equation (4) is transformed into an equation (5) in a matrix form:

$$A\theta=B \qquad (5)$$

wherein $$A = \begin{bmatrix} x_1-x_2 & y_1-y_2 & z_1-z_2 \\ x_2-x_3 & y_2-y_3 & z_2-z_3 \\ x_3-x_4 & y_3-y_4 & z_3-z_4 \end{bmatrix} \qquad (6)$$

$$B = \frac{1}{2}\begin{bmatrix} (x_1^2+y_1^2+z_1^2)-(x_2^2+y_2^2+z_2^2)+d_2^2-d_1^2 \\ (x_2^2+y_2^2+z_2^2)-(x_3^2+y_3^2+z_3^2)+d_3^2-d_2^2 \\ (x_3^2+y_3^2+z_3^2)-(x_4^2+y_4^2+z_4^2)+d_4^2-d_3^2 \end{bmatrix} \qquad (7)$$

The unknown position of the target node is represented as a 3 by 1 matrix $$\theta = \begin{bmatrix} x \\ y \\ z \end{bmatrix}$$

Thus the position of the target node can be represented as:

$$\theta = A^{-1}B \qquad (8)$$

If the positions of more than four reference nodes are known, then the number of unknown parameters is less than the number of equations (m>n), and the accurate position of the target node may be generated using an estimation algorithm. Different iterative algorithms, such as Least Mean-Square Error (LSE) algorithm and Weighted Least Mean-Square Error (WLSE) algorithm, may be adopted.

LSE Algorithm

In equation (5), $A\theta=B$, matrix A is a m*n matrix, and m>n. The error of $\theta$ is set to be r:

$$r=A\theta-B \qquad (9)$$

According to the LSE algorithm, the square of the error needs to be minimized.

$$f(\theta)=(A\theta-B)^T(A\theta-B) \qquad (10)$$

The derivative of equation (10) is solved to find out the limited minimum value, $$\frac{df(\theta)}{d\theta} = 0 \qquad (11)$$

Then $\theta$ is estimated as $$\hat{\theta}=(A^TA)^{-1}A^TB \qquad (12)$$

When m=n, the estimated $\theta=A^{-1}B$.

WLSE Algorithm

In equation (5), $A\theta=B$, and matrix A is a matrix of m*n, and m>n.

The error of $\theta$ is set to be r, and equation (9) is rewritten as $$r=A\theta-B \qquad (9)$$

According to the WLSE theory, the square of the error should be minimized after multiplying the weight.

$$f(\theta)=(A\theta-B)^TW(A\theta-B) \qquad (13)$$

Wherein, W is the weight matrix, which is related to the relevant matrix (Q) of error r.

$$W=Q^{-1} \qquad (14)$$

Then the derivative of equation (13) is solved to find out the limited minimum value, the estimated $\theta$ is $$\hat{\theta}=(A^TWA)^{-1}A^TWB \qquad (15)$$

By means of the distance measurement theory and positioning technique introduced above, the multiple-HWA system in the embodiments described herein can calculate the position of the wireless detector according to the signal strength from the wireless detector, the angle and/or the time of arrival information, wherein the multiple HWAs serve as the reference nodes and the wireless detector serves as the target node.

Figure 5:
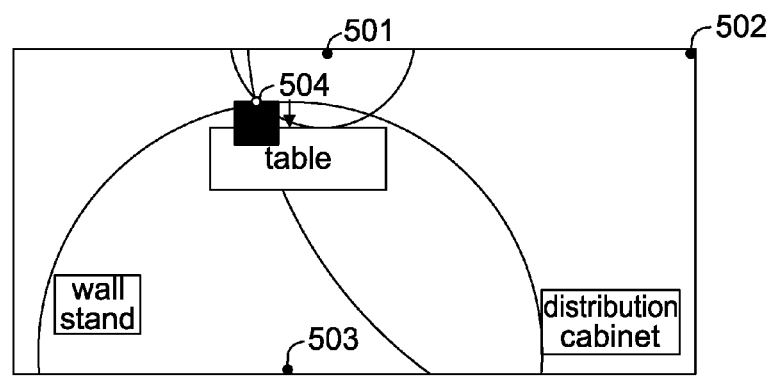
FIG. 5 is a schematic view of an exemplary embodiment of determining a two-dimensional position of a wireless detector.

FIG. 5 is a schematic drawing of determining the two-dimensional position of the wireless detector according to one embodiment, wherein reference numbers 501, 502 and 503 denote three HWAs respectively, and reference number 504 denotes a wireless detector. The three HWAs shown in the figure are all connected with a controller (not shown in the figure). The wireless detector periodically broadcasts beacon messages. For example, the wireless detector may broadcast a UWB beacon every 250 milliseconds. These three HWAs receive the beacon messages from the wireless detector and obtain information about the wireless detector, such as the signal strength of the wireless detector. The controller estimates the distances between the wireless detector and said three HWAs respectively based on the degradation of the signal strength (i.e. the level of signal attenuation), and determines the two-dimensional position of the wireless detector based on the distances between the wireless detector and the three HWAs as well as the positions of these three HWAs. In some embodiments, each of these three HWAs receives the beacon messages from the wireless detector and obtains the time of arrival of the signal of the wireless detector at said HWA. The controller estimates the distances between the wireless detector and said three HWAs respectively based on the time of arrival of the signal of the wireless detector at each HWA, and determines the two-dimensional position of the wireless detector based on the distances between the wireless detector and these three HWAs as well as the positions of the three HWAs.

According to another embodiment, at least four HWAs are arranged in the medical treatment room such as an X-ray exposure room, with at least one HWA being positioned opposite to the insertion direction of the wireless detector, the distance between every two HWAs being smaller than a predetermined value, for example, 5 meters, and the positions of the HWAs being at least 0.5 meter away from a metal obstacle. All the HWAs are connected with a controller. The wireless detector periodically broadcasts beacon messages. For example, the wireless detector may broadcast a UWB beacon every 250 milliseconds. At least four HWAs receive the beacon messages from the wireless detector and obtain information about the wireless detector, such as the signal strength of the wireless detector. The controller estimates the distances between the wireless detector and the at least four HWAs respectively based on the degradation of the signal strength (i.e. the level of signal attenuation), and determines the three-dimensional position of the wireless detector based on the distances between the wireless detector and the at least four HWAs as well as the positions of the at least four HWAs. In some embodiments, each of the at least four HWAs receives the beacon messages from the wireless detector and obtains the time of arrival of the signal of the wireless detector at the HWA. The controller estimates the distances between the wireless detector and the at least four HWAs respectively based on the time of arrival of the signal of the wireless detector at each HWA, and determines the three-dimensional position of the wireless detector based on the distances between the wireless detector and the at least four HWAs as well as the positions of the at least four HWAs.

Where there are a plurality of wireless detectors in the X-ray exposure room, the multiple-HWA system in the embodiments described herein may be used to determine the three-dimensional position of each wireless detector. Since there are a plurality of wireless detectors in the X-ray exposure room, it is necessary to determine the target exposure detector to which the X-ray diagnostic system may inquire image data. In order to determine the target exposure detector, in addition to the three-dimensional position of each of the wireless detectors, it is also necessary to know the position and angle of the X-ray tube. In one embodiment, the angle and position of the X-ray is fed back by an electromechanical device of the X-ray diagnostic system.

After acquiring the three-dimensional positions of the wireless detectors and the position and angle of the X-ray tube, the wireless detector facing the X-ray tube is set as the target exposure detector. If multiple wireless detectors face the X-ray tube, then the first wireless detector along the X-ray beam is set as the target exposure detector. After determining the target exposure detector, the X-ray diagnostic system will automatically inquire image data to the target exposure detector without intervention by the user, thus the whole process of X-ray exposure and data transmission is safer.

It shall be noted that while the position information of the wireless detector is known, it is possible to automatically position the digital cassette, and even to realize a volume radiography of the digital cassette. Automatic tracking and volume radiography have been realized in the X-ray diagnostic system, but they are only applicable to the wall stand and table, and are not applicable to the moving digital cassette mode, because the position and state of the digital cassette is unknown. Once the position of the digital cassette is given, the current design of the X-ray diagnostic system can be applied thereto. Therefore, by applying the above system and method for positioning to the digital cassette, the position of the digital cassette can be obtained, thereby realizing automatic tracking and volume radiography.

While the present invention has been described in detail by specific embodiments, it is not limited to the above-described embodiments. Various modifications and changes can be made to the present invention without departing from the scope of the invention. Therefore, the scope of the present invention is defined by the appended claims.

The invention claimed is:

1. A system for applying a wireless detector in a medical system, comprising:
　at least three host wire adapters configured to:
　　receive beacon messages broadcast periodically by the wireless detector; and
　　obtain information about the wireless detector based on the received beacon messages; and
　a controller configured to:
　　receive information about the wireless detector from said at least three host wire adapters, the information including a respective current signal strength of said at least three host wire adapters;
　　determine a position of the wireless detector based on the received information;
　　compare the respective current signal strengths reported by said at least three host wire adapters to obtain a largest signal strength and to set a host wire adapter corresponding to the largest signal strength as an active host wire adapter;
　　cause the remaining host wire adapters not set as the active host wire adapter to enter a sleep mode; and
　　determine an updated active host wire adapter when the active host wire adapter has a poor link quality due to positioning within a non-line-of-sight range of the wireless detector.

2. The system according to claim 1, wherein the beacon messages are ultra-wide band beacons.

3. The system according to claim 2, wherein the information about the wireless detector includes at least one of angle and time of arrival information.

4. The system according to claim 3, wherein said controller is configured to perform the following operations when the information about the wireless detector includes time of arrival information:
   calculating a time it takes the beacon messages of the wireless detector to arrive at each of said at least three host wire adapters;
   converting the times into distances between the wireless detector and each of said at least three host wire adapters; and
   determining the position of the wireless detector based on the distances and positions of said at least three host wire adapters.

5. The system according to claim 1, wherein said controller is configured to perform the following operations when the information about the wireless detector includes signal strength:
   estimating distances between the wireless detector and said at least three host wire adapters based on a degradation of the respective current signal strengths; and
   determining the position of the wireless detector based on the distances between the wireless detector and said at least three host wire adapters and positions of said at least three host wire adapters.

6. The system according to claim 1, wherein a distance between every two of said at least three host wire adapters is smaller than a predetermined distance.

7. The system according to claim 6, wherein the predetermined distance is 5 meters.

8. The system according to claim 6, wherein said at least three host wire adapters are positioned at corners of a room where the wireless detector is located, and are 2 to 3 meters from a floor and at least 0.3 meters from a ceiling.

9. The system according to claim 1, wherein said controller is further configured to set, when there are a plurality of wireless detectors, a wireless detector facing a radiation source as a target detector according to a position and angle of the radiation source and positions of the plurality of wireless detectors.

10. The system according to claim 9, wherein said controller is further configured to set a first wireless detector along a radiation beam as the target detector when there are more than one wireless detectors facing the radiation source.

11. The system according to claim 10, wherein at least one host wire adapter is positioned opposite to an insertion direction of the target detector.

12. A method for applying a wireless detector in a medical system, comprising:
   obtaining, utilizing at least three host wire adapters, information about the wireless detector based on beacon messages broadcast periodically by the wireless detector, the information including a respective current signal strength of said at least three host wire adapters;
   determining a position of the wireless detector based on the information from the at least three host wire adapters;
   comparing the respective current signal strengths reported by the at least three host wire adapters to obtain a largest signal strength and to set a host wire adapter corresponding to the largest signal strength as an active host wire adapter;
   causing the remaining host wire adapters not set as the active host wire adapter to enter a sleep mode; and
   determine an updated active host wire adapter when the active host wire adapter has a poor link quality due to positioning within a non-line-of-sight range of the wireless detector.

13. The method according to claim 12, wherein the beacon messages are ultra-wide band beacons.

14. The method according to claim 13, wherein the information about the wireless detector is at least one of angle and time of arrival information.

15. The method according to claim 14, wherein when the information about the wireless detector includes time of arrival information, determining a position of the wireless detector comprises:
   calculating a time it takes the beacon messages of the wireless detector to arrive at each of the at least three host wire adapters;
   converting the times into distances between the wireless detector and each of the at least three host wire adapters; and
   determining the position of the wireless detector based on the distances and positions of the at least three host wire adapters.

16. The method according to claim 12, wherein when the information about the wireless detector includes signal strength, determining a position of the wireless detector comprises:
   estimating distances between the wireless detector and the at least three host wire adapters based on a degradation of the respective current signal strengths; and
   determining the position of the wireless detector based on the distances between the wireless detector and the at least three host wire adapters and positions of the at least three host wire adapters.

17. The method according to claim 12, further comprising:
   setting, when there are a plurality of wireless detectors, a wireless detector facing a radiation source as a target detector according to a position and angle of the radiation source and positions of the plurality of wireless detectors.

18. The method according to claim 17, wherein a first wireless detector along a radiation beam is set as the target detector when there are more than one wireless detectors facing the radiation source.

* * * * *